United States Patent [19]
Little et al.

[11] Patent Number: 5,382,674
[45] Date of Patent: Jan. 17, 1995

[54] PREPARATION OF 5-AMINO-1,2,4-TRIAZOLE-3-SULFONA-MIDES

[75] Inventors: Jack C. Little, Lafayette; Mariam G. Kidisti, Pittsburg; Patricia A. Thibos, Concord; Susan D. Thompson, San Leandro, all of Calif.

[73] Assignee: DowElanco, Indianapolis, Ind.

[21] Appl. No.: 287,952

[22] Filed: Dec. 19, 1988

[51] Int. Cl.6 .................................. C07D 249/12
[52] U.S. Cl. ................................... 548/263.8
[58] Field of Search ....................... 548/263.8

[56] References Cited

U.S. PATENT DOCUMENTS

| | | | |
|---|---|---|---|
| 2,554,816 | 5/1951 | Clapp et al. | 548/263.8 |
| 2,744,907 | 5/1956 | Young | 548/263.8 |
| 4,038,387 | 7/1977 | Doyle, Jr. et al. | 548/263.8 |
| 4,226,873 | 10/1980 | Kirkpatrick et al. | 548/263.8 |
| 4,734,123 | 3/1988 | Monte | 548/263.8 |
| 4,755,212 | 7/1988 | Kleschick et al. | 548/263.8 |

FOREIGN PATENT DOCUMENTS

| | | | |
|---|---|---|---|
| 244097A2 | 11/1987 | European Pat. Off. | |
| 268951 | 6/1988 | European Pat. Off. | |
| 3640155 | 5/1988 | Germany | 544/263 |

OTHER PUBLICATIONS

March, Advanced Organic Chemistry, pp. 445, 1087, (1985).
Avetisyan, Arm Khim Zh. 34 781 (1981) Abstract Only.
Abdel–Fattah Egypt J. Chem. 27, 321 (1985) Abstract Only.
R. O. Robin, Jr. and J. W. Clapp, *J. Am Chem. Soc.*, 72, 4890–4892 (1950).
R. G. Shepard, *J. Organic Chem.*, 12, 275–283 (1947).

*Primary Examiner*—Robert Gerstl
*Attorney, Agent, or Firm*—D. Wendell Osborne

[57] ABSTRACT

5-Amino-1,2,4-triazole-3-sulfonamides, which are intermediates for substituted 1,2,4-triazolo-[1,5-a]pyrimidine-2-sulfonamide herbicides are prepared in two steps from 5-amino-3-mercapto-1,2,4-triazole by chlorination in a medium containing an aqueous acid to obtain 5-amino-3-chlorosulfonyl-1,2,4-triazole and subsequent condensation of this intermediate with substituted anilines. The condensation reaction takes place either in the presence or absence of an acid scavenging base.

24 Claims, No Drawings

PREPARATION OF 5-AMINO-1,2,4-TRIAZOLE-3-SULFONAMIDES

BACKGROUND OF THE INVENTION

The present invention relates to a process for the preparation of 5-amino-1,2,4-triazole-3-sulfonamides utilizing 5-amino-3-mercapto-1,2,4-triazole and/or 5-amino-3-chlorosulfonyl-1,2,4-triazole as starting materials or intermediates.

Many 5-amino-1,2,4-triazole-3-sulfonamides, their preparation, and their value as intermediates in the manufacture of substituted 1,2,4-triazolo[1,5-a]-pyrimidine-2-sulfonamide herbicides have been described in U.S. Pat. No. 4,734,123 and 4,755,212. The only process disclosed for preparing these intermediates, however, involves the degradation of 1,2,4-triazolo-[1,5-a]pyrimidine-2-sulfonamide compounds by oxidation to 5-acylamino-1,2,4-triazole-3-sulfonamides and subsequent hydrolysis. This process is very expensive because it involves the preparation and degradation of one 1,2,4-triazolo[1,5-a]pyrimidine-2-sulfonamide compound in order to obtain another 1,2,4-triazolo-[1,5-a]-pyrimidine-2-sulfonamide compound.

The discovery of more direct, lower cost methods for the preparation of intermediates useful in the manufacture of substituted 1,2,4-triazolo[1,5-a]-pyrimidine-2-sulfonamide herbicides would be of great interest.

SUMMARY OF THE INVENTION

It has now been found that 5-amino-1,2,4-triazole-3-sulfonamides, which are valuable intermediates for substituted 1,2,4-triazolo[1,5-a]-pyrimidine-2-sulfonamide herbicides, can be prepared by a process involving the sequential steps of chlorination of the readily available 5-amino-3-mercapto-1,2,4-triazole to obtain 5-amino-3-chlorosulfonyl-1,2,4-triazole as an intermediate and subsequent condensation of this intermediate with substituted anilines. The individual steps in the process can be practiced independently.

The chlorination step of the process is carried out by contacting 5-amino-3-mercapto-1,2,4-triazole with chlorine in a medium containing an aqueous acid under conditions conducive to the formation of 5-amino-3-chlorosulfonyl-1,2,4-triazole (Formula II).

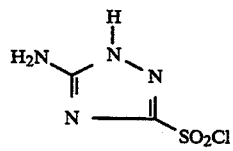

FORMULA II in the condensation step of the process, a 5-amino-1,2,4-triazole-3-sulfonamide of Formula I

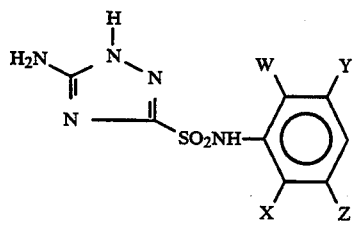

FORMULA I wherein

W represents F, Cl, Br, I, $R^1$, $SR^1$, $SOR^1$, $SO_2R^{R1}$, $CO_2R^2$, CN, or $NO_2$;

X represents H, F, Cl, Br, I, $R^1$, $CH_2OR^1$, $OR^1$, $CO_2R^2$, $NO_2$ or a phenyl, phenoxy, or 2-pyridinyloxy group each optionally containing up to 3 compatible substituents selected from F, Cl, Br, $CH_3$, and $CF_3$;

Y represents H, F, Cl, Br, I, $R^1$, or $CO_2R^2$;

Z represents H, F, Cl, Br, I, or $R^1$;

$R^1$ represents $C_1$–$C_4$ alkyl optionally containing one or more chloro or fluoro substituents; and $R^2$ represents H, $C_1$–$C_4$ alkyl, $C_3$–$C_4$ alkenyl, or $C_3$–$C_4$ alkynyl, each optionally containing up to four compatible substituents selected from chloro, fluoro, $OR^1$, and phenyl is prepared by contacting 5-amino-3-chlorosulfonyl-1,2,4-triazole of Formula II with a substituted aniline of Formula III

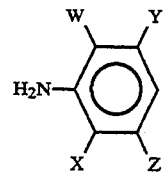

FORMULA III wherein W, X, Y, and Z are as defined hereinabove under conditions conducive to the formation of a compound of Formula I.

One preferred process utilizing conditions conducive to the formation of a compound of Formula I from the compound of Formula II and a compound of Formula III is to contact approximately equimolar amounts of the two reactants in a suitable organic solvent in the substantial absence of added acid acceptor.

The two steps of the process can be carried out consecutively without separation and recovery of the intermediate of Formula II if the reaction media are selected to be compatible. It is preferred to employ acetic acid or formic acid in the reaction medium in this embodiment of the invention.

The 5-amino-1,2,4-triazole-3-sulfonamides of Formula I prepared can be converted to substituted 1,2,4-triazolo[1,5-a]pyrimidine-2-sulfonamide herbicides by condensation with 1,3-dicarbonyl compounds using procedures known in the art.

5-Amino-3-chlorosulfonyl-1,2,4-triazole is an intermediate which is an important aspect of the invention.

DETAILED DESCRIPTION OF THE INVENTION

The overall process of the present invention takes advantage of the availability and low cost of 5-amino-3-mercapto-1,2,4-triazole (a compound that possesses several possible tautomeric forms and is alternately named 5-amino-2,4-dihydro-3H-1,2,4-triazole-3-thione), which is well known in the art, as a starting material for the preparation of substituted 1,2,4-triazolo[1,5-a]pyrimidine-2-sulfonamide herbicides. The process of the invention involves several separate chemical reaction steps. These reaction steps can be carried out in sequence to obtain the desired herbicidal products. Alternately, the separate steps can be carried out individually and independently, for example, to prepare the intermediate 5-amino-3-chlorosulfonyl-1,2,4-triazole (Formula II) from 5-amino-3-mercapto-1,2,4-triazole, to prepare 5-amino-1,2,4-triazole-3-sulfonamides (Formula I) from 5-amino-3-chlorosulfonyl-1,2,4-triazole, or to prepare a substituted 1,2,4-triazolo[1,5-a]pyrimidine-2-
-sulfonamide from either of these compounds as an
intermediate or as a starting material.

5-Amino-3-chlorosulfonyl-1,2,4-triazole (Formula II)
can be obtained by chlorination of 5-amino-3-mercapto-
1,2,4-triazole under conditions conducive to the conversion. The reaction can be depicted as follows:

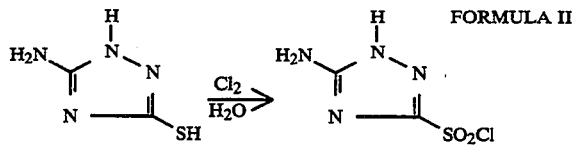

FORMULA II

The conversion is generally effected by treating the
5-amino-3-mercapto-1,2,4-triazole with chlorine in an
aqueous acid medium until the reaction is substantially
complete. Agitation is generally employed to promote
contact of the reagents.

The temperature is generally maintained in the range
of about the freezing point of the mixture to about 50°
C.. It is preferably maintained at about $-10°$ C. to about
30° C. and more preferably at about 0° C. to about 25°
C.. External cooling is generally employed as the reaction is exothermic.

The reaction theoretically requires three moles of
chlorine per mole of the 5-amino-3-mercapto-1,2,4-
triazole. Chlorine amounts of from about 2.8 to about
3.6 moles per mole of 5-amino-3-mercapto-1,2,4-triazole
are typically employed and amounts of about 2.9 to
about 3.2 are preferred. Chlorine is usually added until
uptake virtually ceases, which occurs at about 3 moles,
since the reaction generally takes place about as fast as
the chlorine can be added.

The reaction generates hydrochloric acid as a by-product and hydrochloric acid is, therefore, always present
during the process. Acids are also generally employed
in the initial reaction medium. Suitable acids that can be
employed include strong mineral acids, such as hydrochloric, sulfuric, and phosphoric acids, and organic
acids, such as formic, acetic, propionic, trifluoroacetic,
and methanesulfonic acids. The acids can be employed
in combination. Suitable acids are those that facilitate
the conversion of a 3-mercapto group to a 3-chlorosulfonyl group, but do not unduly catalyze hydrolysis or
extrusion of sulfur dioxide or other undesirable reactions of the product of Formula II and whose aqueous
mixtures are liquid solutions. It is generally preferred to
employ aqueous hydrochloric acid.

About 1 to about 37 percent hydrochloric acid is
typically employed as the chlorination medium. It is
often preferred to employ initial hydrochloric acid concentrations of about 5 percent to about 30 percent and
more preferred to employ initial concentrations of
about 10 to about 25 percent. The medium increases in
acid concentration during the reaction due to the production of hydrochloric acid as a by-product.

When the reaction is carried out in a medium containing an aqueous carboxylic acid, such as formic or acetic
acid, the initial medium can be varied between acid
containing about 1.5 moles of water per mole of 5-
amino-3-mercapto-1,2,4-triazole and mixtures of water
and carboxylic acid containing about 50 percent water.
Acetic acid is a preferred carboxylic acid. It is often
preferred to employ acetic acid containing about 2 (the
theoretical amount) to about 10 moles of water per
mole of 5-amino-3-mercapto-1,2,4-triazole or to employ
mixtures of water and acetic acid containing about 10 to
about 50 percent the acid. Hydrochloric acid is often
advantageously employed in conjunction with the carboxylic acid. In one procedure about one mole of hydrochloric acid is employed per mole of 5-amino-3-mercapto-1,2,4-triazole.

An amount of aqueous acid containing medium is
generally employed so that the concentration of 5-
amino-3-mercapto-1,2,4-triazole is at about 5 to about 40
percent weight/volume percent medium. Unreactive
organic solvents can be employed in combination with
the aqueous acid.

The 5-amino-3-chlorosulfonyl-1,2,4-triazole formed
can be recovered as a wet solid containing some hydrochloric acid by conventional means, such as by filtration
or centrifugation. It is best recovered quickly after the
chlorine addition is complete and then quickly used as is
or dried in order to avoid yield losses due to hydrolysis
or sulfur dioxide evolution.

The condensation of compounds of Formula II with
substituted anilines of Formula III to obtain compounds
of Formula I wherein W represents F, Cl, Br, I, $R^1$,
$SR^1$, $SOR^1$, $SO_2R^1$, $CO_2R^2$, CN, or $NO_2$; X represents
H, F, Cl, Br, I, $R^1$, $CH_2OR^1$, $OR^1$, $CO_2R^2$, $NO_2$, or a
phenyl, phenoxy, or 2-pyridinyloxy group each optionally containing up to 3 compatible substituents selected
from F, Cl, Br, $CH_3$, and $CF_3$; Y represents H, F, Cl, Br,
I, $R^1$, or $CO_2R^2$; Z represents H, F, Cl, Br, I, or $R^1$; $R^1$
represents $C_1$–$C_4$ alkyl optionally containing one or
more chloro or fluoro substituents; and $R^2$ represents H,
$C_1$–$C_4$ alkyl, $C_3$–$C_4$ alkenyl, or $C_3$–$C_4$ alkynyl, each
optionally containing up to four compatible substituents
selected from chloro, fluoro, $OR^1$ and phenyl is effected
by allowing the two starting materials to react under
conditions conducive to the formation of the compound
of Formula I. The reaction can be depicted as follows:

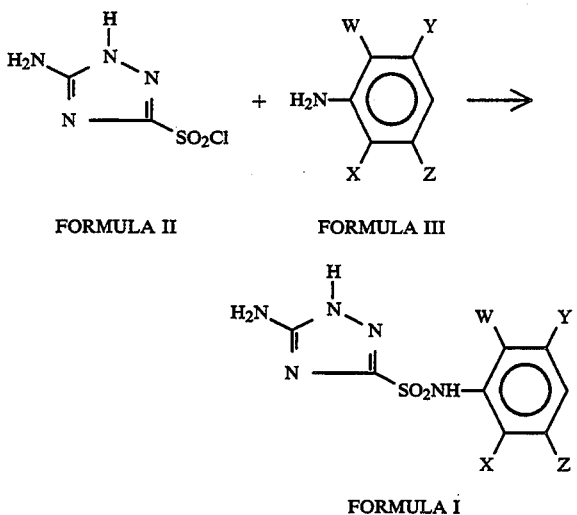

FORMULA II        FORMULA III

FORMULA I

The process is sometimes conducted by combining
appropriate compounds of Formulas II and III in the
presence of an organic solvent and an acid scavenging
base and heating with agitation until a recoverable
amount of the compound of Formula I is obtained.
Approximately equimolar quantities of the two reactants or about a 100 percent excess or more of the substituted aniline are generally employed in this variation.
Tertiary amine bases, including pyridine type bases, such as pyridine and methylated pyridines, trialkylamines, such as triethylamine and N-methylmorpholine, and dialkylarylamines, such as dimethylaniline, can be employed as the acid scavenging base. Certain inorganic bases, including alkali metal salts of carboxylic acids, such as sodium acetate, and alkali metal carbonates, such as potassium carbonate, are also sometimes employed. A second mole of substituted aniline can also sometimes be employed as the acid scavenging base. The acid scavenging bases are typically used in approximately equimolar amounts to the compound of Formula II in this procedure, but may be used in excess.

It has been found, however, that it is not necessary to employ an acid scavenging base in the condensation process. The reaction proceeds when the two reactants are combined in a suitable solvent under conditions conducive to the condensation reaction and allowed to react until a recoverable amount of the compound of Formula I is formed. This is a surprising and often preferred procedure. It has the advantages of obviating the need to recover and recycle an acid scavenging base, of being less sensitive to protic impurities, such as water, in the system, of being less susceptible to degradation of the 5-amino-3-chlorosulfonyl -1,2,4-triazole reactant, of simplifying the recycle of unreacted substituted aniline reactant and, as a result, of giving higher yields of purer product. About 0.9 mole to about 1.2 mole of substituted aniline of Formula III per mole of 5-amino-3-chlorosulfonyl -1,2,4-triazole (Formula II) is generally employed when this method is employed. Mole ratios of about 0.9 to about 1.1 are sometimes preferred.

It is possible in this procedure to use as the starting material 5-amino-3-chlorosulfonyl-1,2,4-triazole that has been recovered from its preparation medium, but not dried and, consequently, contains some water and some hydrochloric acid.

The product that forms when no acid acceptor is employed is the hydrochloride salt of a compound of Formula I. This product can be recovered as the free base by adjusting the pH of the medium to between about 4.5 and 6.5. It can, however, also be recovered as the hydrochloride salt when a solvent in which the hydrochloride salt is not highly soluble, such as acetonitrile, is employed. The insoluble or slightly soluble product is simply separated from the reaction medium by conventional means, such as by filtration or centrifugation. Good yields are obtained and, in addition, any unreacted starting materials can be recycled with the solvent. This procedure is often preferred.

Suitable solvents for the condensation reaction, whether employing an acid acceptor or not, are those that at least slightly dissolve the reactants and which do not adversely affect the reaction. Suitable solvents include, for example, acetonitrile, propionitrile, sulfolane, benzonitrile, formic acid, propionic acid and acetic acid. Acetonitrile or acetic acid are often preferred. The process is usually conducted with agitation in a substantially dry medium when acid scavenging bases are employed, but may contain a small amount of water when they are not.

Temperatures of about 25° C. to about 125° C. are generally employed and temperatures of about 50° C. to about 90° C. are preferred. The reaction is typically complete in about 1 hour to about 6 days and more often in about 2 to about 24 hours.

The product of Formula I can be recovered by conventional means, such as by extracting the product into an aqueous alkaline medium and then reprecipitating it from that medium with acid (final pH of about 4.5 to 6.5) and recovering the solid product by filtration or centrifugation. Water and excess acid can be removed by heating in a conventional drier.

It is sometimes possible to combine the steps of chlorination of 5-amino-3-mercapto-1,2,4-triazole to obtain 5-amino-3-chlorosulfonyl-1,2,4-triazole and condensation of that intermediate with a substituted aniline of Formula III without recovery of the intermediate 5-amino-3-chlorosulfonyl-1, 2,4-triazole. This embodiment of the invention is advantageous in that it reduces the number of operations involved in the overall process, the recycle of solvents, and the amount of waste generated. The embodiment is usually carried out by conducting the chlorination in a medium comprising formic acid or acetic acid containing about 2 to about 4 moles of water per mole of 5-amino-3-mercapto-1,2,4-triazole. The condensation step of the process is often preferably carried out using about 1 mole of 5-amino-3-chlorosulfonyl-1,2,4-triazole to about 0.9 to about 1.2 moles of substituted aniline and no acid scavenging base. It is also often carried out in the presence of an approximately equimolar amount or an excess of a compatible acid scavenging base, such as sodium acetate or pyridine, or in the presence of excess substituted aniline. Each of the steps of the process can be carried out essentially as described hereinabove, except that the by-product hydrochloric acid and, optionally, any excess water must be taken into account. Both hydrochloric acid and water are preferably removed by distillation or evaporation under reduced pressure before proceeding to the next step. Alternately, one or more of the indicated acid scavenging bases, including excess substituted aniline of Formula III can be added to neutralize any acid before proceeding.

The compounds of Formula I can be condensed with 1,3-dicarbonyl compounds to obtain the herbicidal substituted 1,2,4-triazolo[1,5-a]pyrimidine-2-sulfonamide herbicides of Formula IV disclosed in U.S. Pat. No. 4,755,212.

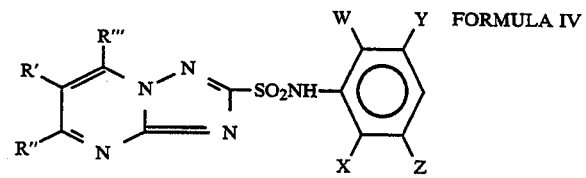

FORMULA IV

The condensation can be carried out as described in U.S. Pat. Nos. 4,734,123 and 4,755,212, the appropriate portions of which are hereby incorporated by reference. The compound of Formula I is typically employed in a recovered and dried form, but it may also be employed as a wet solid or without being recovered from the medium in which it was prepared. In the latter case the pH of the medium is generally adjusted to an appropriate value before proceeding.

The following examples are presented to illustrate the invention and should not be construed as limiting the scope of the invention. All melting points are uncorrected. High pressure liquid chromatography (HPLC) analyses were made using a Spectra-Physics Model SP8490 detector, SP8800 pump, and SP4290 integrator system equipped with a 25 cm Rainin C-18 80-225-C5 reverse phase column eluting with 30:70 acetonitrile:water, buffered with 0.05M ammonium dihydrogen phosphate, 0.05M ammonium formate, 0.05M trifluoroacetic acid, or 0.01N sulfuric acid, at a flow rate of 1 ml/min and monitoring at a wave length of 230 nm or an essentially equivalent system.

EXAMPLE 1.

Preparation of 5-Amino-3-chlorosulfonyl -1,2,4-triazole (Formula II)

5-Amino-3-mercapto-1,2,4-triazole (58 g, 0.50 mole) and 400 ml of 10 percent aqueous hydrochloric acid were placed in a reaction vessel equipped with a fritted gas inlet tube, stirrer, thermometer, and gas outlet which was immersed in a dry ice/isopropyl alcohol bath. When the temperature of the mixture dropped to −10° C., chlorine was added through the gas addition tube with stirring and cooling. In all 113 g (1.6 moles) was added over a 50 min period at −7 to −11° C. The initial slurry became thin and then thick again and the color changed first to a yellow-orange and then back to pale yellow. The resulting slurry was allowed to warm to 15° C. over a 1 hour period and was then filtered to collect the solids. This solid appeared to dissolve in water with some gas evolution and then reprecipitate as an orange solid. It was recovered by filtration and air dried to obtain 16.8 g (18 percent of theory) of the title compound melting at 157.5°–158° C.(dec.).

Elemental analysis: Calc. for $C_2H_3ClN_2O_2S$: %C, 13.2; %H, 1.66; %N, 30.7 Found: %C, 13.2; %H, 1.79; %N, 30.5

The carbon-13 nmr spectrum had absorptions at 161.5 and 158.8 ppm, tentatively assigned to the carbon atoms at the 3- and 5- positions, respectively. The compound in hot aqueous hydrochloric acid decomposed to 5-amino-3-chloro-1,2,4-triazole and sulfur dioxide and hydrolyzed to 5-amino-1,2,4-triazole-3-sulfonic acid, a compound decomposing on heating at above 330° C. These compounds had nmr spectra consistent with the assigned structures.

The title compound was obtained in similar preparations in various hues from snow white through orange and melting with decomposition (gas evolution) at temperatures up to 172° C.

EXAMPLE 2.

Preparation of 5-Amino-3-chlorosulfonyl -1,2,4-triazole (Formula II)

A 1 liter bottom draining glass reactor fitted with a fritted glass gas inlet tube, a gas outlet with a sulfuric acid scrubber, a paddle stirrer, a thermometer, and a jacket connected to a recirculating temperature regulated bath maintained at 18° C. A mixture containing 116 g (1.0 mole) of 5-amino-3-mercapto-1,2,4-triazole and 800 ml of 20 percent aqueous hydrochloric acid (made from 432 ml of 37 percent hydrochloric acid and 368 ml of water) was placed in the reactor and 222 g (3.13 moles) of chlorine was added thorough the gas inlet tube with stirring and cooling over a 165 min period. The temperature of the mixture was maintained at about 22 to about 32° C. under these conditions. The color of the mixture was changeable in the pale yellow to orange range and the initial slurry first thinned out and then became thick again as the reaction proceeded. After all the chlorine was added (uptake and the exotherm ceased), the temperature was reduced to about 5° C. and the mixture was removed though the bottom drain. The solids were collected by filtration, washed with 500 ml of cold water, and air dried to obtain the title compound as a pale yellow solid melting at 169.5°–170° C. (dec.). This amounted to 124 g (68 percent of theory) and was found by HPLC analysis to be about 95.5 percent of the title compound and about 4.5 percent 5-amino -1,2,4-triazole-3-sulfonic acid. The filtrate and wash were found by HPLC analysis to contain additional amounts of the title Compound.

EXAMPLE 3

Preparation of 5-Amino-N-(2,6-difluoro Phenyl)-1,2,4-triazole-3-sulfonamide ( Formula I, W and X=F, Y and Z=H)

A mixture of 6.5 g (0.05 mole) of 2,6-difluoroaniline, 9.6 g (0.05 mole) of 5-amino-3-chlorosulfonyl -1,2,4-triazole and 40 ml of acetonitrile was stirred at about 70° C. for a total of 5 days. The resulting colorless slurry was taken up in a mixture of 30 ml of 10 percent aqueous sodium hydroxide and 170 ml of water and washed with 2×100 ml of methylene chloride to remove traces of unreacted aniline. The aqueous phase was then warmed to about 60° C., acidified to pH 4.5 and chilled to 2° C. The solids that formed were collected by filtration, washed with cold water, and dried overnite in air to obtain 13.0 g (89 percent of theory) of the monohydrate of the title aminotriazolesulfonamide, m.p. 230° C. (dec.), and after off-gassing and refreezing 254°–255° C. (dec.). HPLC analysis showed only a single peak. The proton and carbon nmr spectra were identical with those of an authentic sample.

EXAMPLE 4.

Preparation of 5-Amino-N-(2,6-dichloro-3-methylphenyl)-1,2,4-triazole-3-sulfonamide (Formula I, W and X=Cl, Y=CH$_3$, and Z=H)

In a manner similar to that described in Example 3, 8.8 g (0.05 mole) of 2,6-dichloro-3-methylaniline, 9.6 g (0.05 mole) of 5-amino-3-chlorosulfonyl -1,2,4-triazole and 25 ml of dry acetonitrile were stirred at about 65° C. for a total of 5 days. The reaction product was recovered as in Example 3 to obtain 10.8 g of the title compound as white solid, m.p. 240°–241° C. (dec.). This assayed by HPLC to be about 98 percent pure. The methylene chloride washes were concentrated to obtain 2.7 g of solid which was over 80 percent purity unreacted 2,6-dichloro-3-methylaniline. The yield of the desired sulfonamide was therefore 88 percent based on unrecovered aniline.

The following compounds of Formula I were prepared, recovered, and analyzed similarly:

5-Amino-N-(2,3-dimethyl-6-nitrophenyl)1,2,4-triazole -3-sulfonamide (W and Y=CH$_3$, X=NO$_2$, and Z=H), m.p. 115°–116° C.;

5-Amino-N-(2,6-dichlorophenyl)-1,2,4-triazole-3-sulfonamide (W and Y=Cl, X and Z=H), m.p. 115°–116° C.; and 5-Amino-N-(2-carboxymethyl-6-fluorophenyl )-1,2,4-triazole-3-sulfonamide (W=CO$_2$CH$_3$, X=F, and Y and Z=H), m.p. 233°–234° C.

EXAMPLE 5

Preparation of 5-Amino-N-(2,6-difluorophenyl) -1,2,4-triazole-3-sulfonamide (Formula I, W and X=F, Y and Z=H)

5-Amino-3-chlorosulfonyl-1,2,4-triazole (20 g of about 92 percent purity, 0.1 mole) was slurried in 168 g (2.8 moles) of acetic acid and 14.2 g (0.11 moles) of 2,6-difluoroaniline were added. The mixture was stirred and heated at 90° C. for 11 hours at which time analysis by HPLC a 76 percent conversion to the title compound and 9 percent conversion to its 5-acetylamino derivative. Water was added and the mixture cooled to 10° C. The solids were collected by filtration, washed with water, and dried at 60° C. to obtain 14.8 g (53 percent of theory) of the title compound as a 96 percent purity product. Analysis of the filtrate by HPLC showed that it contained another 26 percent of theory and the total yield was 79 percent of theory.

EXAMPLE 6

Preparation of 5-Amino-N-(2,6-chloro-3-methylphenyl)-1,2,4,triazole-3-sulfonamide (Formula I, W and X=Cl, Y=CH$_3$, and Z=H)

5-Amino-3-chlorosulfonyl-1,2,4-triazole (9.1 g, 0.050 mole) was slurried in 15 ml of acetic acid and 8.8 g (0.050 moles) of 2,6-dichloro-3-methylaniline were added. The mixture was stirred and heated at 70° C. for 5 hours. Another 50 ml of acetic acid was added and the mixture heated with stirring for 30 min at 90° C. at which time the 5-amino-3-chlorosulfonyl-1,2,4 -triazole was essentially gone by HPLC analysis. The mixture was allowed to cool and water was added. The solids present were collected by filtration, washed with water, and placed in 200 ml of 5 percent aqueous sodium hydroxide. The insoluble fraction, which was unreacted 2,6-dichloro-3-methylaniline, was removed by filtration. The filtrate, which contained the title compound contaminated with its 5-acetylamino derivative, was heated at reflux for 6 hours, allowed to cool, and acidified with concentrated aqueous hydrochloric acid to pH 4.5. The solid that formed was recovered by filtration, washed with water, and dried in a vacuum oven overnight to obtain 11.5 g (67 percent of theory) of the title compound as a 93.5 percent purity product containing about 4.5 percent residual water as determined by HPLC analysis.

EXAMPLE 7

Preparation of 5-Amino-N-(2,6-chloro-3-methylphenyl)-1,2,4-triazole-3-sulfonamide (Formula I, W and X=Cl, Y=CH$_3$, and Z=H) from 5-Amino-3-mercapto-1,2,4-triazole Chlorine (37 g, 0.52 mole) was passed into a stirring mixture of 20 g (0.17 mole) of 5-amino-3-mercapto-1,2,4-triazole slurried in 181 g (3 moles) of acetic acid containing 17.8 g of concentrated aqueous hydrochloric acid (0.17 mole of hydrochloric acid and 0.63 mole of water) over a 30–40 min period with cooling by means of an external bath to maintain the temperature at about 5–15° C. The mixture was allowed to react for several hours at about 10° C. at which time HPLC analysis indicated about 88 percent conversion to 5-amino-3-chlorosulfonyl-1,2,4-triazole. Volatiles were then removed by evaporation under reduced pressure at up to 50° C. until about 80 g of residue remained. 2,6-Dichloro-3-methylaniline (41 g, 0.23 mole) was added and the mixture allowed to react with stirring at 25°–60° C. for about 47 hours, at which time about 11 percent of the 5-amino-3-chlorosulfonyl-1,2,4-triazole remained, and then for another 48 hours at about 60° C. Analysis of the mixture by HPLC indicated that it contained 0.10 mole of the title compound which corresponds to a yield of about 59 percent of theory. The mixture was steam distilled to remove excess 2,6-dichloro-3-methylaniline and volatile impurities. The solids were recovered by filtration and dried to obtain 32.5 g of 93 percent (by HPLC) purity title compound (53 percent of theory) as a white solid.

EXAMPLE 8

Preparation of 5-Amino-N-(2,6-fluorophenyl)-1,2,4-triazole-3-sulfonamide (Formula I, W and X=F, Y and Z=H) from 5-Amino-3-mercapto-1,2,4-triazole Chlorine (79 g, 1.1 mole) was passed into a stirring mixture of 37 g (0.32 mole) of 5-amino-3-mercapto-1,2,4-triazole slurried in 250 g of acetic acid containing 18 g of concentrated aqueous hydrochloric acid (0.19 mole of hydrochloric acid and 0.62 mole of water) over a 3.6 hour period with cooling by means of an external bath to maintain the temperature at about 6°–22° C. When the reaction appeared to be complete 100 g of acetic acid and other volatiles were removed by evaporation under reduced pressure at temperatures up to about 36°–39° C. A small amount of water (12 g, 0.66 mole) and then 40 g (0.32 mole) of 2,6-difluoroaniline were added with stirring at 40° C. over a 30 min period. The temperature was increased to 65° C. and the reaction continued for about 95 min. Water (150 g) was then added and the resulting mixture cooled to about 2° C. and filtered. The solids obtained were washed with water and dried overnight at 60° C. in a vacuum oven to obtain 39 g (47 percent of theory) of the title compound assaying 99 percent purity by HPLC.

EXAMPLE 9

Preparation of 5-Amino-N-(2,6-difluorophenyl-1,2,4-triazole-3sulfonamide Hydrochloride (Formula I, W and X=F, Y and Z=H, as the Hydrochloride)

A mixture of 65 g (0.50 mole) of 2,6-difluoroaniline, 96 g (0.50 mole) of about 95 percent purity 5-amino-3-chlorosulfonyl-1,2,4-triazole and 400 ml of acetonitrile was heated at reflux (about 84° C.) for a total of 17 hours with stirring over most of the period (not all due to a power failure). The resulting slurry of a white solid in an orange-brown liquid was chilled to about 5° C. and the solids were recovered by filtration, extracted with 3×200 ml of acetonitrile to remove the orange color, and dried to obtain 121 g (76 percent of theory) of the title compound as a granular white solid, m.p. 219° C. (dec.) (authentic sample 224°–225° C. (dec.)). HPLC analysis indicated about 97 percent purity. HPLC analysis of the liquid phase and the first extract indicated that they contained another approximately 8 percent yield of the title compound and some unreacted 2,6-difluoroaniline.

EXAMPLE 10

Preparation of 5-Amino-N-(2,6-difluorophenyl-1,2,4-triazole-3-sulfonamide Hydrochloride (Formula I, W and X=F, Y and Z=H, as the Hydrochloride)

A mixture of 60.0 g ( 0.465 mole ) of 2,6-difluoroaniline, 96.1 g (0.50 mole) of 5-amino-3 -chlorosulfonyl-1,2,4-triazole and 400 ml of dry acetonitrile was heated with stirring. After an initial exotherm to 78° C., the mixture was maintained at 70° C. for 23 hours. It was then chilled to 3° C. and filtered to recover the title compound as a white, highly crystalline solid, which, after washing with 150 ml of cold acetonitrile and drying, melted at 214°–217° C. (dec.). This was found to be about 96.0 percent pure by HPLC and the major impurity was found to be 5-amino -1,2,4-triazole-3-sulfonic acid. An additional 0.8 g of the title compound that deposited on standing was recovered similarly, m.p. 219°–221° C.

The combined mother liquors from the above reaction were combined with 48.0 g (0.372 mole) of 2,6-difluoroaniline and 89.4 g (0.465 mole) of 5-amino--3-chlorosulfonyl-1,2,4-triazole and the reaction repeated. The title compound was obtained as a white, crystalline solid of about 91 percent purity melting at 216°–217° C. (dec.) and amounting to 126.2 g. This procedure was repeated and 130.4 g of the title compound was obtained as a white, crystalline solid of about 90 percent purity melting at 208°–209° C. (dec.).

The total recovered yield of the title compound from the above sequence was 93.4 percent based on 2,6-difluoroaniline and 79 percent based on 5-amino-3-chlorosulfonyl-1,2,4-triazole, after correcting for assays.

What is claimed is:

1. A process for preparing a 5-amino-1,2,4-triazole-3-sulfonamide compound of the formula

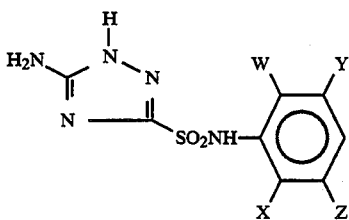

wherein
W represents F, Cl, Br, I, $R^1$, $SR^1$, $SOR^1$, $SO_2R^1$, $CO_2R^2$, CN, or $NO_2$;
X represents H, F, Cl, Br, I, $R^1$, $CH_2OR^1$, $OR^1$, $CO_2R^2$, $NO_2$, or a phenyl, phenoxy, or 2-pyridinyloxy group each optionally containing up to 3 compatible substituents selected from F, Cl, Br, $CH_3$, and $CF_3$;
Y represents H, F, Cl, Br, I, $R^1$, $CO_2R^2$;
Z represents H, F, Cl, Br, I, or $R^1$;
$R^1$ represents $C_1$–$C_4$ alkyl optionally containing one or more chloro or fluoro substituents; and
$R^2$ represents H, $C_1$–$C_4$ alkyl, $C_3$–$C_4$ alkenyl, or $C_3$–$C_4$ alkynyl, each optionally containing up to four compatible substituents selected from chloro, fluoro, $OR^1$, and phenyl
which comprises the consecutive steps of
a) contacting 5-amino-3-mercapto-1,2,4-triazole with chlorine in a medium containing an aqueous acid under conditions conducive to the formation of 5-amino-3-chlorosulfonyl-1,2,4-triazole

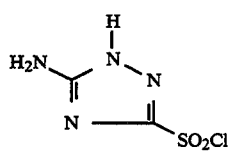

and
b) contacting 5-amino-3-chlorosulfonyl-1,2,4-triazole with a substituted aniline of the formula

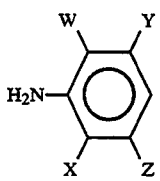

wherein W, X, Y, and Z are as defined hereinabove under conditions conducive to the formation of said 5-amino-1,2,4-triazole-3-sulfonamide compound.

2. A process according to claim 1 wherein acetic acid containing about 2 to about 4 moles of water per mole of 5-amino-3-mercapto-1,2,4-triazole is employed in the medium in step a and steps a and b are carried out without recovery of the 5-amino-3-chlorosulfonyl-1,2,4-triazole prepared from the mixture obtained in step a.

3. A process according to claim 1 wherein in step b about 0.9 to about 1.2 mole of substituted aniline per mole of 5-amino-3-chlorosulfonyl-1,2,4-triazole is employed in the substantial absence of additional acid scavenging base.

4. A process according to claim 3 wherein the 5-amino-1,2,4-triazole-3-sulfonamide is recovered as its hydrochloride salt.

5. A process for preparing 5-amino-3-chlorosulfonyl-1,2,4-triazole which comprises contacting 5-amino-3-mercapto-1,2,4-triazole with chlorine in a medium containing an aqueous acid under conditions conducive to the formation of 5-amino-3-chlorosulfonyl-1,2,4-triazole.

6. A process according to claim 5 wherein the medium contains one or more of aqueous hydrochloric acid, acetic acid, and formic acid.

7. A process according to claim 6 wherein the medium contains about 1 to about 37 percent aqueous hydrochloric acid.

8. A process according to claim 7 wherein the medium contains about 5 to about 30 percent aqueous hydrochloric acid.

9. A process according to claim 5 wherein the medium contains aqueous acetic acid or formic acid.

10. A process according to claim 9 wherein the medium contains about 2 to about 4 moles of water per mole of 5-amino-3-mercapto-1,2,4-triazole.

11. A process according to claim 10 wherein the 5-amino-3-chlorosulfonyl-1,2,4-triazole prepared is employed as an intermediate without recovery from the reaction mixture obtained.

12. A process according to claim 5 wherein the temperature is between about $-10°$ C. and about 30° C.

13. A process for preparing a 5-amino-1,2,4-triazole-3-sulfonamide compound of the formula

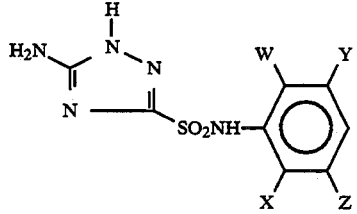

wherein
W represents F, Cl, Br, I, $R^1$, $SR^1$, $SOR^1$, $SOR_2R^1$, $CO_2R^2$, CN or $NO_2$;

X represents H, F, Cl, Br, I, $R^1$, $CH_2OR^1$, $OR^1$, $CO_2R^2$, $NO_2$, or a phenyl, phenoxy, or 2-pyridinyloxy group each optionally containing up to 3 compatible substituents selected from F, Cl, Br, $CH_3$, and $CF_3$;

Y represents H, F, Cl, Br, I, $R^1$, or $CO_2R^2$;

Z represents H, F, Cl, Br, I, or $R^1$;

$R^1$ represents $C_1$–$C_4$ alkyl optionally containing one or more chloro or fluoro substituents; and $R^2$ represents H, $C_1$–$C_4$ alkyl, $C_3$–$C_4$ alkenyl, or $C_3$–$C_4$ alkynyl, each optionally containing up to four compatible substituents selected from chloro, fluoro, $OR^1$, and phenyl which comprises contacting 5-amino-3-chlorosulfonyl-1,2,4-triazole with a substituted aniline of the formula

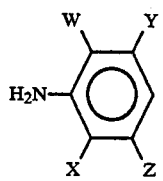

wherein W, X, Y, and Z are as defined hereinabove under conditions conducive to the formation of said 5-amino-1,2,4-triazole-3-sulfonamide compound.

14. A process according to claim 13 wherein about 0.9 to about 1.2 moles of substituted aniline per mole of 5-amino-3-chlorosulfonyl-1,2,4-triazole is employed in the substantial absence of additional acid scavenging base.

15. A process according to claim 14 wherein the 5-amino-1,2,4-triazole-3-sulfonamide is recovered as its hydrochloride salt.

16. A process according to claim 14 wherein an organic solvent in which the reactants are at least slightly soluble and which do not adversely affect the reaction is employed.

17. A process according to claim 16 wherein the organic solvent is selected from acetic acid and acetonitrile.

18. A process according to claim 14 wherein the reaction is conducted at a temperature of about 50° C. to about 90° C.

19. A process according to claim 13 wherein an acid scavenging base is employed.

20. A process according to claim 19 wherein organic solvent in which the reactants are at least slightly soluble and which do not adversely affect the reaction is employed.

21. A process according to claim 20 wherein the organic solvent is selected from acetic acid and acetonitrile.

22. A process according to claim 19 wherein the reaction is conducted at a temperature of about 50° C. to about 90° C.

23. A process according to claim 19 wherein an alkali metal salt of a carboxylic acid is employed as the acid scavenging base.

24. A process according to claim 19 wherein an excess of substituted aniline is employed as the acid scavenging base.

* * * * *